US00PP30724P2

(12) United States Plant Patent
Hanna et al.

(10) Patent No.: US PP30,724 P2
(45) Date of Patent: Jul. 16, 2019

(54) GRASS NAMED 'TIFT H18'

(50) Latin Name: *Pennisetum alopecuroides*
Varietal Denomination: Tift H18

(71) Applicant: University of Georgia Research Foundation, Inc., Athens, GA (US)

(72) Inventors: Wayne W. Hanna, Chula, GA (US); Brian M. Schwartz, Tifton, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 15/932,491

(22) Filed: Mar. 6, 2018

(51) Int. Cl.
*A01H 5/12* (2018.01)
*A01H 5/02* (2018.01)

(52) U.S. Cl.
USPC ..... Plt./384
CPC ..... *A01H 5/12* (2013.01); *A01H 5/02* (2013.01)

(58) Field of Classification Search
USPC ..... Plt./384
CPC ..... A01H 5/12; A01H 5/02; A01H 5/00
See application file for complete search history.

(56) References Cited

PUBLICATIONS

Restricted Testing Agreement for 'Tift H18' (identified as "*Pennisetum alopecuroides* H-18" in this Restricted Testing Agreement); effective Feb. 22, 2012; redacted to eliminate: (a) the identity of the recipient of 'Tift H18' plant material under this Restricted Testing Agreement; and (b) non 'Tift H18' varieties; 4 pages.

*Primary Examiner* — Kent L Bell
(74) *Attorney, Agent, or Firm* — Klarquist Sparkman, LLP

(57) ABSTRACT

A new variety of *Pennisetum alopecuroides* plant named 'Tift H18' produces a reduced number of seeds, making it less invasive.

2 Drawing Sheets

Latin name of the genus and species of the plant claimed: 'Tift H18' is a vegetatively propagated ornamental perennial *Pennisetum* cultivar of the genus and species *Pennisetum alopecuroides*.

Variety denomination: The new *Pennisetum alopecuroides* claimed is of the cultivar denominated 'Tift H18'.

BACKGROUND OF THE INVENTION

The present invention relates to a new and distinct cultivar of *Pennisetum alopecuroides* herein referred to as 'Tift H18'.

The new *Pennisetum alopecuroides* is a product of a planned research, evaluation, and testing program conducted by the Inventors in Tifton, Ga. The objective of the *Pennisetum alopecuroides* research program is to create a new plant cultivar with reduced seed production. This cultivar is commercially important for its superior ornamental value and low seed production. These and other qualities are enumerated herein.

Pedigree and history: *Pennisetum alopecuroides* accessions and cultivars are known to produce abundant seed. Seed production in commercial ornamental cultivars of *Pennisetum alopecuroides* tends to make this genus/species invasive, an undesirable trait in landscapes. In the summer of 2008, we harvested open-pollinated seed from vegetatively propagated plants of *Pennisetum alopecuroides* var. *Hameln* growing in the field at Tifton, Ga. We established plants from the 2008 open-pollinated seed in a greenhouse in spring 2009 and transplanted 400 of these plants to a field in May 2009. Fifty of these 400 plants with the best morphological characteristics were selected and open-pollinated seed was harvested in 2010 from these fifty plants. In 2010, we irradiated half of the harvested open-pollinated seed with 10 Kr and the other half of these seeds with 15 Kr Cobalt 60 gamma radiation. These irradiated seeds were planted in a field in 2010 to produce 323 plants; 169 plants from the 10 Kr treated seed and 154 plants from the 15 Kr treated seed. Eleven plants out of these 323 plants with one or no seed per inflorescence were selected. Irradiation of seeds usually results in chimeras or sectors on the plants for the trait of interest. Therefore, each of these 11 selected plants was divided into four quadrants or sectors (a, b, c, and d) and five or more inflorescences from each quadrant of each plant were examined for seed sterility.

We determined that six (numbered 1 through 6) of these selected eleven plants had desirable ornamental and morphological characteristics. These six plants were asexually propagated by stem propagules from the a, b, c, and d quadrants on the plants and transplanted to the field in 2011. As many propagules as possible were obtained from each quadrant. Inflorescences from plants from six propagules from quadrant b of plant 4 of plants 1-6 (plant 4 being a plant from one of the 15 Kr treated seed) set various amounts of seed, but a plant from one propagule (field entry 133) produced no seed and became 'Tift H18'. 'Tift H18' has been tested at Tifton, Ga. in 2012, 2014, and 2015 and at Blairsville, Ga. in 2013 and 2015. Tests consisted of five and four single plant replications arranged in a randomized complete block experiment at Tifton, Ga. and Blairsville, Ga., respectively. Seven other experimental entries were included in each test. 'Tift PA24' was selected as a seed fertile check with desirable ornamental characteristics from Tift PS1122. 'Tift PA24' also produced abundant pollen for pollinating the experimental seed sterile cultivars in the replicated tests to make sure that the experimental sterile cultivars would not set seed when pollinated with pollen from another genotype. We selected 'Tift PA24' as the seed fertile check Asexual reproduction of the new *Pennisetum* 'Tift H18' by vegetative propagation (single stem propagules) in a controlled environment in Tifton, Ga. and Blairsville, Ga. from 2012 through 2015, has shown that the unique features of this new *Pennisetum* cultivar are stable and reproduced true to type in successive generations.

SUMMARY OF THE INVENTION

The following traits have been repeatedly observed and represent the characteristics of a new *P. alopecuroides* cultivar 'Tift H18'. The new cultivar 'Tift H18' has not been observed under all possible environmental conditions. The phenotype may vary somewhat with variations in, for example, temperature, day-length, light intensity, soil types, and water and fertility levels without, however, any variance in genotype.

Throughout this specification, color names beginning with a small letter signify that the name of that color, as used in common speech, is aptly descriptive. Color names beginning with a capital letter designate values based upon The R.H.S. Colour Chart (5$^{th}$ Edition, 2007), published by The Royal Horticultural Society, London, England.

The following traits have been repeatedly observed for the new *P. alopecuroides* cultivar 'Tift H18' in Tifton, Ga. and Blairsville, Ga. and can be compared to *P. alopecuroides,* 'Tift PA24' (a seed and pollen fertile genotype with desirable ornamental characteristics):

1. 'Tift H18' is highly seed sterile.

The new cultivar *Pennisetum* 'Tift H18' can be compared to *Pennisetum alopecuroides*, 'Tift PA24', a seed fertile and desirable ornamental selection:

Plants of the new *Pennisetum* 'Tift H18' are compared to 'Tift PA24' in the following characteristics:

1. The new cultivar 'Tift H18' produces significantly fewer seeds at Tifton, Ga. and Blairsville, Ga. compared to 'Tift PA24'.
2. The new cultivar 'Tift H18' produces inflorescences and leaf heights significantly shorter than 'Tift PA24'.
3. The new cultivar 'Tift H18' produces a leaf canopy diameter that is significantly narrower than 'Tift PA24'.
4. In Tifton, Ga., but not in Blairsville, Ga., inflorescence lengths of the new cultivar 'Tift H18' are significantly shorter than those of 'Tift PA24'.
5. Leaf width and length of the new cultivar 'Tift H18' are significantly smaller than 'Tift PA24'.
6. The new cultivar 'Tift H18' generally produces significantly fewer inflorescences than 'Tift PA24'.

The following observations, measurements, and values describe plants grown in Tifton, Ga. and Blairsville, Ga. In Tables 1-7, the least significant difference (LSD) is set at P≤0.05 probability level. Growth days were included in ratings. Plants were spaced 1 meter apart down the row and rows were 2 meters apart. Plants were established as single stem propagules in mid-April to mid-May and rated in September through October. Data was taken from plants during year of establishment at Tifton, Ga. and Blairsville, Ga. except 2015 data from Blairsville was taken on plants established in 2014.

'Tift H18' plants were narrower in canopy diameter and significantly shorter than 'Tift PA24' in height of inflorescences and in height of leaves, and canopy diameter. Except for one year in Tifton, Ga., 'Tift H18' had significantly fewer inflorescences that 'Tift PA24' (Table 4); and shorter inflorescences than 'Tift PA24' in Tifton, Ga. (Table 5). Leaf length and width values were significantly less for 'Tift H18' compared to 'Tift PA24' (Table 6). 'Tift H18' is a finer textured and more petite plant than 'Tift PA24'. These features are of major interest to commercial propagators.

Mature plant color of the adaxial leaf surface of 'Tift H18' was Green-139B according to the Royal Horticultural Society color index (5$^{th}$ Edition, 2007), whereas inflorescence colors were Greyed Orange-165C for 'Tift H18'.

Seed set in 'Tift H18' is significantly reduced.

TABLE 1

Height of inflorescence of two *Pennisetum alopecuroides* grasses ('Tift PA24' is the seed and pollen fertile control) planted at two locations in Georgia.

| | Height of Inflorescence | | | | |
|---|---|---|---|---|---|
| | Tifton | | | Blairsville | |
| Entry | 2012 | 2014 | 2015 | 2013 | 2015 |
| 'Tift H18' | 28 | 30 | 39 | 70 | 53 |
| 'Tift PA24' | 62 | 51 | 83 | 126 | 106 |
| LSD | 6 | 9 | 8 | 12 | 9 |
| Growth Days | 180 | 99 | 101 | 116 | 155 |

Plant heights were measured from ground level to top of inflorescence. The Tifton tests were planted 18 Apr. 2012, 2 Jun. 2014, and 12 May 2015 and measurements were taken 15 Oct. 2012, 9 Sep. 2014, and 21 Aug. 2015, respectively. The Blairsville tests were planted 16 May 2013, and 15 May 2014, and measurements were taken 9 Sep. 2013 and 24 Sep. 2015 (data taken on 2014 plants), respectively. The least significant difference at the P≤0.05 probability level. Measurements are in centimeters.

TABLE 2

Height of leaves of two ornamental *Pennisetum alopecuroides* grasses ('Tift PA24' is the seed and pollen fertile control) planted at two locations in Georgia.

| | Height of Leaves | | | | | |
|---|---|---|---|---|---|---|
| | Tifton | | | | Blairsville | |
| Entry | 2012 | 2013 | 2014 | 2015 | 2013 | 2015 |
| 'Tift H18' | 49 | 12 | 20 | 20 | 55 | 33 |
| 'Tift PA24' | 86 | 41 | 34 | 54 | 73 | 83 |
| LSD | 9 | 8 | 7 | 5 | 9 | 5 |
| Growth Days | 180 | 170 | 99 | 101 | 116 | 155 |

The height of leaves were measured from ground level to top of leaf canopy. The tests at Tifton were planted 18 Apr. 2012, 13 Apr. 2013, 2 Jun. 2014, and 12 May 2015 and measurements taken 5 Oct. 2012, 30 Sep. 2013, 9 Sep. 2014, and 21 Aug. 2015, respectively. The Blairsville tests were 16 May 2013, and 15 May 2014, and measurements were taken 9 Sep. 2013 and 24 Sep. 2015 (data taken on 2014 plants), respectively. The least significant difference at the P≤0.05 probability level. Measurements are in centimeters.

TABLE 3

Canopy diameter of two ornamental *Pennisetum alopecuroides* grasses ('Tift PA24' is the seed and pollen fertile control) planted at two locations in Georgia.

| | Canopy Diameter (cm) | | |
|---|---|---|---|
| | Tifton | | Blairsville |
| Entry | 2012 | 2015 | 2015 |
| 'Tift H18' | 62 | 61 | 55 |
| 'Tift PA24' | 81 | 98 | 136 |
| LSD | 10 | 9 | 7 |
| Growth Days | 180 | 101 | 155 |

The canopy diameter is the average diameter of the widest and the narrowest diameter of a single plant canopy. The tests at Tifton were planted 18 Apr. 2012 and 12 May 2015 and measurements taken 8 Oct. 2012, and 21 Aug. 2015, respectively. The test at Blairsville were planted 15 May 2014 and measurements taken 24 Sep. 2015(data taken on 2014 plants). The least significant difference was set at the P≤0.05 probability level.

TABLE 4

Number of inflorescences per plant of two ornamental *Pennisetum alopecuroides* grasses ('Tift PA24' is the seed and pollen fertile control) planted at two locations in Georgia.

| | Number of Inflorescences | | | |
|---|---|---|---|---|
| | Tifton | | | Blairsville |
| Entry | 2012 | 2014 | 2015 | 2015 |
| 'Tift H18' | 14 | 61 | 63 | 44 |
| 'Tift PA24' | 79 | 135 | 62 | 67 |
| LSD | 33 | 42 | 16 | 19 |
| Growth Days | 180 | 99 | 101 | 155 |

Total number of inflorescences were counted per plant. The tests at Tifton were planted 18 Apr. 2012, 13 Apr. 2013, 2 Jun. 2014, and 12 May 2015 and measurements were taken on 15 Oct. 2012, 30 Sep. 2013, 9 Sep. 2014, and 21 Aug. 2015, respectively. The test at Blairsville were planted 15 May 2014, and measurements were taken 0 24 Sep. 2015 (data taken on 2014 plants), respectively. The least significant difference was set at the P≤0.05 probability level.

TABLE 5

Inflorescence length of two ornamental *Pennisetum alopecuroides* grasses ('Tift PA24' is the seed and pollen fertile control) planted at two locations in Georgia.

| | Inflorescence Length (cm) | | |
|---|---|---|---|
| | Tifton | | Blairsville |
| Entry | 2012 | 2015 | 2015 |
| 'Tift H18' | 9 | 8.8 | 15 |
| 'Tift PA24' | 13 | 11.1 | 15 |
| LSD | 1 | 0.8 | 1.4 |
| Growth Days | 180 | 101 | 155 |

Inflorescence length was the mean of three inflorescences per plant. The tests at Tifton were planted 18 Apr. 2012 and 12 May 2015 and measurements taken 15 Oct. 2012 and 21 Aug. 2015, respectively. The tests at Blairsville were planted 14 Apr. 2012, 16 May 2013, and 15 May 2014, and measurements taken 9 Sep. 2012, 9 Sep. 2013, 22 Sep. 2014 and 24 Sep. 2015 (data taken on 2014 plants), respectively. The least significant difference at the P≤0.05 probability level.

TABLE 6

Leaf characteristics of individual plants of two ornamental *Pennisetum alopecuroides*grasses ('Tift PA24' is the seed and pollen fertile control) planted at two locations in Georgia.

| | Leaf Length (cm) | | | Leaf Width (mm) | | |
|---|---|---|---|---|---|---|
| | Tifton | | Blairsville | Tifton | | Blairsville |
| Entry | 2012 | 2015 | 2015 | 2012 | 2015 | 2015 |
| Tift H18' | 21.0 | 21.0 | 28.3 | 3.7 | 4.6 | 3.8 |
| 'Tift PA24' | 26.8 | 33.6 | 40.2 | 6.5 | 7.4 | 9.6 |
| LSD | 5.1 | 3.3 | 10.9 | 1.4 | 0.7 | 1.1 |

Leaf length (average from three culms) was measured from the leaf collar to the leaf tip of the latest fully extended leaf. Leaf width (average of three culms) was measured in the center of the latest fully extended leaf. The tests at Tifton were planted 18 Apr. 2012 and 12 May 2015 and measurements taken 15 Oct. 2012, and 21 Aug. 2015, respectively. The tests at Blairsville were planted 15 May 2014 and measurements taken 24 Sep. 2015 (data taken on 2014 plants), respectively. The least significant difference was set at the P≤0.05 probability level.

TABLE 7

Seed Set per inflorescence and seed germination of six ornamental *Pennisetum alopecuroides* grasses ('Tift PA24' is the seed and pollen fertile control) planted at two locations in Georgia.

| | Seeds per Inflorescence | | | Seed Germination - % |
|---|---|---|---|---|
| | Tifton | | Blairsville | Blairsville |
| Entry | 2013 | 2015 | 2015 | 2015 |
| 'Tift H18' | 0.3 | 0.0 | 0.1 | 48 |
| 'Tift PA24' | 15.4 | 91.5 | 71.2 | 93 |
| LSD | 0.3 | 0.0 | 1.3 | 21 |

Seeds per inflorescence was the mean of four random inflorescences per each replication. Seed germination tests consisted of 25 seeds from four and three different plants (replications) harvested in October 2014 at Tifton and Blairsville, respectively. Germination tests were conducted in April of 2015 to allow seeds to go through a dormancy period and simulate field conditions. The Tifton tests were planted 13 Apr. 2013 and 12 May 2015 and measurements taken in October 2013 and 2015. The Blairsville test was planted 15 May 2014, and measurements taken 24 Sep. 2015 (data taken on 2014 plants), respectively. The least significant differences were set at the P≤0.05 probability level.

TABLE 8

Summary of morphological characteristics of two *Pennisetum alopecuroides* cultivars

| Trait | 'Tift PA24' | 'Tift H18' |
|---|---|---|
| Mature inflorescence height | 51-126 cm | 28-70 cm |
| Mature leaf height | 34-86 cm | 12-55 cm |
| Diameter of plant canopy | 81-135 cm | 55-62 cm |
| Inflorescence length | 11.1-15 cm | 9-15 cm |
| Number of Inflorescences per plant | 62-135 | 14-63 |
| Leaf width | 7.4-9.6 mm | 3.7-4.6 mm |
| Leaf length | 26.8-40.2 cm | 21-28.3 cm |
| Adaxial leaf surface trichomes | Glabrous | Glabrous |
| Abaxial leaf surface trichomes | Glabrous | Glabrous |
| Leaf blade margin trichome length | Less than 0.5 mm long | Sparse, less than 0.5 mm long |
| Leaf collar trichomes long | Dense, 2 mm long | Medium density, 1 mm |
| Sheath trichomes | Margins sparse, 1 mm long | Glabrous |
| Ligule | Yes. | Yes |
| Ligule trichomes | Sparse, less than 1 mm long | 1 mm long |
| Sheath trichomes | Sparse, 1 mm long | Glabrous |
| Floret length | 5-6 mm | 5 mm |
| Bristle length surrounding florets | 6-19 mm | 4-15 mm |

BRIEF DESCRIPTION OF THE FIGURES

The accompanying colored photographs illustrate the overall appearance and distinct characteristics of the new cultivar of *Pennisetum* 'Tift H18'. The colors in the photographs are as close as possible with the photographic and printing technology utilized.

Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to the Royal Horticultural Society (RHS) Colour Chart ($5^{th}$ edition, 2007).

DETAILED DESCRIPTION

Figure 1:
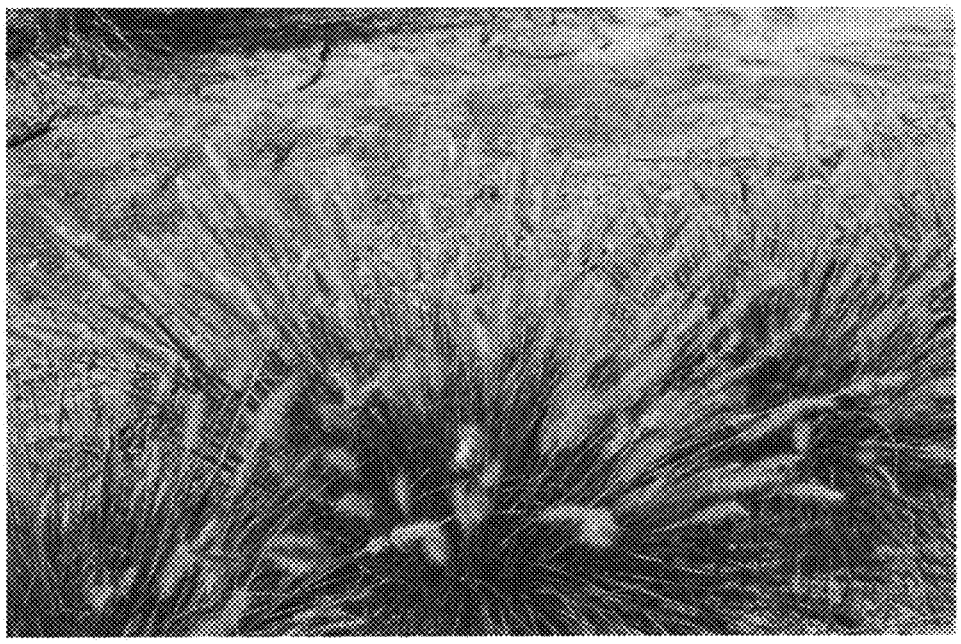
FIG. 1 is a photograph of a 'Tift H18' plant at anthesis in a research plot (year of establishment) in Tifton, Ga.
Figure 2:
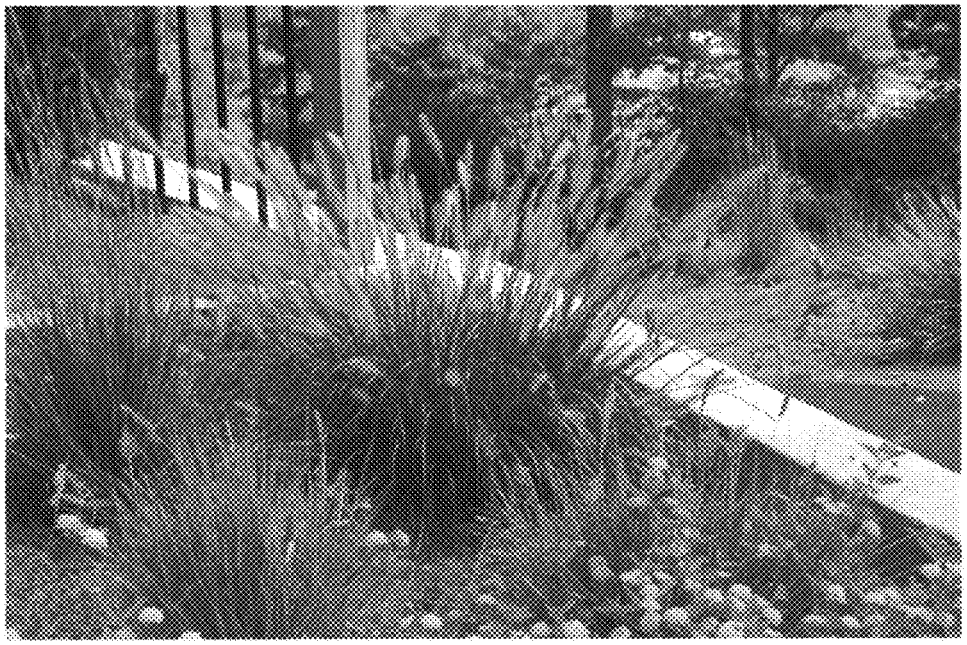
FIG. 2 is a photograph of a 'Tift H18' plant at anthesis in yard (year of establishment) in Union County Ga.

The new cultivar 'Tift H18' is a vigorous perennial at Blairsville, Ga. (USDA Zone 7a). The new cultivar 'Tift H18' survived 90, 95, and 101 days below 0° C. and low temperatures of −9, −29, and −17° C. for the winters of 2012/2013, 2013/2014, and 2014/2015, respectively at Blairsville, Ga. in a landscape setting where no herbicides were used.

All data are from plants established as single stem propagules in mid-April to mid-May and rated in September through October, except 2015 data from Blairsville, Ga. was collected from plants established in 2014.

Plant:

*Mature inflorescence height.*—28-70 cm.

*Mature leaf height.*—12-55 cm.

*Diameter of plant canopy.*—55-62 cm.

*Inflorescence length.*—9-15 cm.

*Number of Inflorescences per plant.*—14-63.

Leaf:

*Number of culms per plant.*—Number is approximately the same as the number of inflorescences per plant (see Table 4), because most of the major culms produce an inflorescence.

*Leaf width.*—3.7-4.6 mm.

*Leaf length.*—21-28.3 cm.

*Adaxial leaf surface trichomes.*—Glabrous.

*Abaxial leaf surface trichomes.*—Glabrous.

*Leaf blade margin trichome length.*—Sparse, less than 0.5 mm long.

*Leaf collar trichomes.*—Medium density, 1 mm long.

*Sheath trichomes.*—Glabrous.

*Ligule.*—Yes.

*Ligule trichomes.*—1 mm long.

*Sheath trichomes.*—Glabrous.

*Adaxial leaf color.*—Green 139B.

*Abaxial leaf color.*—Green 139D.

*Inflorescence color.*—Greyed Orange 165C.

*Disease susceptibility.*—Although rust (*Puccinia substriata*), leaf spot (*Pyricularia grisea*), and *Helminthosporium* sp. leaf spot are common diseases for *Pennisetum* in Tifton, Ga. due to its humid and warm climate; to date, 'Tift H18' has not presented any disease symptoms.

*Pest susceptibility.*—No pest susceptibility has been observed for 'Tift H18'.

*Hardiness.*—'Tift H18' has survived 64, 97, and 96 d below 0° C. and low temperatures of −12° C., −18° C., and −17° C., in 2012, 2014, and 2015, respectively in Blairsville, Ga.

The invention claimed is:

1. A new and distinct cultivar of *Pennisetum alopecuroides* plant named 'Tift H18', as illustrated and described herein.

* * * * *